(12) United States Patent
Rémigy et al.

(10) Patent No.: US 9,116,091 B2
(45) Date of Patent: Aug. 25, 2015

(54) PREPARATION OF CRYOGENIC SAMPLE FOR CHARGED-PARTICLE MICROSCOPY

(71) Applicant: FEI Company, Hillsboro, OR (US)

(72) Inventors: Hervé-William Rémigy, Eindhoven (NL); Karin Smulders-Weemers, Helmond (NL); Mikhail Mikhaylovich Ovsyanko, Eindhoven (NL); Frank Nijpels, Veldwezelt (BE); Kasim Stefan Sader, Doorwerth (NL)

(73) Assignee: FEI COMPANY, Hillsboro, OR (US)

( * ) Notice: Subject to any disclaimer, the term of this patent is extended or adjusted under 35 U.S.C. 154(b) by 0 days.

(21) Appl. No.: 14/498,712

(22) Filed: Sep. 26, 2014

(65) Prior Publication Data

US 2015/0090878 A1    Apr. 2, 2015

(30) Foreign Application Priority Data

Sep. 30, 2013    (EP) .................................... 13186632

(51) Int. Cl.
| | |
|---|---|
| *H01J 37/00* | (2006.01) |
| *G01N 1/42* | (2006.01) |
| *H01J 37/26* | (2006.01) |
| *H01J 37/20* | (2006.01) |

(52) U.S. Cl.
CPC . *G01N 1/42* (2013.01); *H01J 37/20* (2013.01); *H01J 37/26* (2013.01); *H01J 2237/002* (2013.01)

(58) Field of Classification Search
CPC ......... G01N 1/42; G01N 1/2813; H01J 37/20; H01J 37/26; H01J 2237/002

USPC ..................... 250/306, 307, 310, 311, 440.11
See application file for complete search history.

(56) References Cited

FOREIGN PATENT DOCUMENTS

EP    2381236 A1 * 10/2011

* cited by examiner

*Primary Examiner* — Michael Maskell
(74) *Attorney, Agent, or Firm* — Scheinberg & Associates, PC; Michael O. Scheinberg

(57) ABSTRACT

A method of preparing a sample for a charged-particle microscope includes:

Providing a substantially plate-like sample holder having opposed first and second major surfaces substantially parallel to one another, comprising at least one aperture connecting said major surfaces and across which a membrane has been spanned upon said first major surface, which membrane comprises at least one perforation;

Spanning a film of liquid across said perforation, which liquid comprises at least one study specimen suspended therein;

Plunging the sample holder onto a bath of cryogen, whereby the sample holder is held with said first major surface pointing toward the cryogen and arranged substantially parallel to an exposed surface of the cryogen; and Applying a blast of cryogenic fluid to said film from a nozzle pointing toward said second major surface, immediately prior to the film making contact with said cryogen.

A corresponding apparatus is also described.

20 Claims, 8 Drawing Sheets

PREPARATION OF CRYOGENIC SAMPLE FOR CHARGED-PARTICLE MICROSCOPY

The invention relates to a method of preparing a sample for study in a charged-particle microscope, comprising the following steps:

Providing a substantially plate-like sample holder having opposed first and second major surfaces substantially parallel to one another, comprising at least one aperture that connects said major surfaces and across which a membrane has been spanned upon said first major surface, which membrane comprises at least one perforation;

Spanning a film of aqueous liquid across said perforation, which liquid comprises at least one study specimen suspended therein;

Plunging the sample holder onto a bath of cryogen, whereby the sample holder is held with said first major surface pointing toward the cryogen and arranged substantially parallel to an exposed surface of the cryogen.

The invention additionally relates to an apparatus for plunge-cooling a sample for study in a charged-particle microscope, which sample is provided on a substantially planar sample holder, the apparatus comprising:

An arm that can be used to grip an edge of said sample holder and retain it in a substantially horizontal orientation;

A container that can be at least partially filled with a bath of cryogen, such that said cryogen has an exposed upper surface at a given horizontal level;

A dropping mechanism that can be used to move said arm into said container, allowing a sample holder in said arm to be plunged below said horizontal level, with a frontside of the sample holder pointing downward.

The invention also relates to a method of examining a sample in a charged-particle microscope, which microscope comprises:

A charged-particle source for producing a beam of charged particles;

A supporting device for supporting a sample holder on which the sample is mounted;

A cooling device for maintaining said sample holder at a cryogenic temperature at least while it is on said supporting device;

A particle-optical column for directing said beam onto and through said sample, so as to form an image of part of the sample on a detector As used throughout this text, the ensuing terms should be interpreted consistent with the following explanation:

The phrase "charged particle" encompasses an electron or ion (generally a positive ion, such as a Gallium ion or Helium ion, for example, although a negative ion is also possible; the ion in question may be a charged atom or molecule). The term may also refer to a proton, for example.

The term "microscope" refers to an apparatus that is used to create a magnified image of an object, feature or component that is generally too small to be seen in satisfactory detail with the naked human eye. In a charged-particle microscope (CPM), an imaging beam of charged particles is directed onto a sample using a so-called "particle-optical column", which comprises a collection of electrostatic and/or magnetic lenses that can be used to manipulate said beam, serving to provide it with a certain focus or deflection, for example, and/or to mitigate one or more aberrations therein. In certain types of CPM, a different particle-optical column may also be used to focus charged particles emanating from the sample onto a detector. In addition to imaging, a CPM may also have other functionalities, such as performing spectroscopy, examining diffractograms, performing (localized) surface modification (e.g. milling, etching, deposition), etc.

The substantially plate-like sample holder may comprise more than one of the described apertures; in particular, it may be a grid-like structure that contains a matrix arrangement of such apertures. Similarly, the membrane spanned across a given aperture may contain more than one of the described perforations; in particular, it may comprise a (random or regular) distribution of such perforations. The perforations themselves may be deliberately created (e.g. using a boring, pricking, punching or etching technique), or they may be naturally present in the membrane. Pre-manufactured, disposable, grid-like sample holders as described here are commercially available to users of CPMs.

The phrase "aqueous liquid" is intended to encompass pure liquid water, but also water-based solutions or suspensions. The term therefore includes electrolytes, in addition to biological liquids such as cytoplasm, blood plasma, lymphatic fluid or amniotic fluid, for example.

The aqueous liquid film is essentially "spanned" across said perforation(s) with the aid of surface tension effects. There are known methods in the prior art for performing this procedure, e.g. using a sheet of blotting paper that is pressed against the sample holder, moistened with the aqueous liquid in question, and then removed—leaving a thin film of aqueous liquid behind in the perforation(s), somewhat analogous to a soapy film in the ring of a bubble blower.

The term "cryogen" should be interpreted as referring to a liquid at cryogenic temperatures, i.e. at or below −150° C.

The "sample" in the current case may be regarded as being said spanned film of (solidified) aqueous liquid, including its suspended study specimen(s). In practice, a CPM study performed on such a sample will generally tend to concentrate on said specimen(s) rather than on the (solidified) liquid in which they are encapsulated.

In what follows, the invention will—by way of example—often be set forth in the specific context of electron microscopes. However, such simplification is intended solely for clarity/illustrative purposes, and should not be interpreted as limiting.

Charged-particle microscopy is a well-known and increasingly important technique for imaging microscopic objects, particularly in the form of electron microscopy. Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example. In a TEM, the electron beam used to irradiate a sample will generally be of significantly higher energy than in the case of a SEM (e.g. 300 keV vs. 10 keV), so as to allow its constituent electrons to penetrate the full depth of the sample; for related reasons, a sample investigated in a TEM will also generally need to be thinner than one investigated in a SEM. In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example.

Since the imaging electron beam in a TEM penetrates a sample under investigation, such a sample needs to be relatively thin (as already stated above) and also needs to be mounted on a sample holder that does not appreciably interfere with said electron beam. These requirements can present significant challenges in the case of certain types of sample. In particular, biological specimens (such as cells, cell components, single-cellular organisms, etc.) that need to be stored and studied in a body of aqueous liquid (such as water, electrolyte, cell fluid, blood plasma, etc.) can present significant challenges vis-à-vis their examination in a CPM, since:

An aqueous liquid introduced into a (quasi-)vacuum environment of a CPM will start to outgas/boil, thus tending to degrade the sample;

In order to prevent this, the sample can first be frozen before being introduced into said vacuum;

However, so as to prevent damage to the sample caused by the formation of (sharp) ice crystals, such freezing must generally be performed very rapidly, with the aim of achieving sample vitrification (solidification into an amorphous, glass-like phase) without significant ice crystallization;

A sample resulting from this vitrification process should be sufficiently thin to be efficiently penetrated by the impinging beam in the CPM, but one should be able to support it by its edges—or at least on a very thin (portion of the) sample holder—so that the means of support have no—or at least relatively limited—effect on beam penetration.

These requirements tend to turn the preparation of such samples into a significant technological challenge.

A method as set forth in the opening paragraph above is elucidated in the article *Vitrification of cryoelectron microscopy specimens revealed by high-speed photographic imaging* by S. Kasas et al., J. Microscopy 211(1), July 2003, pp. 48-53. This article is basically interested in studying stroboscopically analyzed, time-resolved thermal contact profiles between a grid-like sample holder (3 mm-diameter copper grid, carbon membrane, aperture size typically 70-200 μm, perforation size 2 μm, typical pitch of ~1-5 μm between perforations) and a cryogen bath into which it is plunged. In this regard, it discusses the difference between "vertical plunging" of the sample holder into a cryogen (whereby the plane of the sample holder is perpendicular to an exposed surface of the cryogen) and "horizontal plunging" (whereby the plane of the sample holder is parallel to an exposed surface of the cryogen), and it proposes the latter as a way of achieving a more uniform vitrification result than the former (in terms of more homogeneous heat transfer from the sample to the cryogen). However, the article does not (substantially) concern itself with other important aspects of the sample preparation and, in particular, fails to address the subject of sample contamination.

In studies preceding the invention, the inventors noticed that the "horizontal plunging" method alluded to above consistently tended to produce samples that suffered from significant contamination. See, for example, FIG. 3A below, which shows a 1 μm×1 μm square portion of a vitrified sample obtained using prior-art techniques. At the employed magnification (~30 k), this square should essentially be a quasi-uniform grey color (since the aforementioned study specimens in the sample are too small to be resolved in this image); however, as can clearly be seen from the Figure, the sample is instead covered by a distribution of dark, dot-like features. The presence of these contaminant features can greatly hinder subsequent analysis of the sample in a CPM, since they act as scattering sites for the CPM's imaging beam of charged particles. If a particular study specimen happens to be located along a shared line-of-sight with such a contaminant feature, or proximal thereto, then it generally cannot be satisfactorily viewed using the CPM.

It is an object of the invention to address the issues set forth above. In particular, it is an object of the invention to provide a sample vitrification procedure in which the occurrence of the abovementioned contamination issues is mitigated.

These and other objects are achieved in a method as set forth in the opening paragraph above, which method is characterized in that it applies a blast of cryogenic fluid to said film from a nozzle pointing toward said second major surface, immediately prior to the film making contact with said cryogen.

In experiments leading to the invention, the inventors closely investigated the contaminant features discussed above. Using TEM tomography, they were able to ascertain that the features occurred on the "backside" of the sample, i.e. the side facing away from the cryogen bath during horizontal plunging. Compositional analysis revealed the contaminant features to be surficial islands of water ice that had somehow managed to form while other parts of the sample were vitrifying. After much further investigation, the inventors arrived at the conclusion that liquid water present in the sample itself was leaching out of the sample backside as the frontside of the sample contacted the cryogen bath, and this leaching water was freezing into surficial ice (before it could be amorphously solidified inside the sample by the bath). Armed with this realization, the inventors sought a way of preventing such leaching from occurring. They eventually arrived at the insight that, by applying a sudden blast of cryogenic fluid to the backside of the sample just prior to the instant of contact between the cryogen bath and the sample's frontside, the backside of the sample could be vitrified, thus forming a barrier to liquid water that might otherwise leach out of the sample. The result of this inventive procedure was a dramatic reduction in the occurrence of the hitherto widespread contaminant features—as illustrated in FIG. 3B, for example, which shows a 1 μm×1 μm square portion of a vitrified sample obtained using the present invention, which is essentially free of the contaminant features that are prevalent in FIG. 3A.

In the context of the current invention, the following should be noted:

As regards the cryogenic fluid that is blasted at the backside of the aqueous film, the term "fluid" should be broadly interpreted as encompassing a gas or liquid, or hybrid forms such as a spray or vapor, for example, and the term "cryogenic" should (once again) be interpreted as referring to a temperature at or below −150° C.

The cryogenic fluid in the blast and the cryogen in the plunging bath do not have to (but, if desired, may nevertheless) have the same composition/temperature. For example, the cryogen might be liquid ethane at a temperature of −178° C., whereas the cryogenic fluid might be substantially dry nitrogen gas at a temperature of −160° C. (and <10 ppm water; ppm=parts per million).

The term "nozzle" should be broadly interpreted as referring to any dosing apparatus that is capable of delivering a temporally defined dose of cryogenic fluid. Such temporal definition may, for example, be achieved with the aid of a controllable valve or shutter, and/or using a mechanism that can rapidly move a nozzle into/out of position above the sample backside. The timing/duration of the blast may, for example, be dictated by (setpoints generated by) an automated mechanism used to plunge the sample holder into the cryogen. For convenience, a tube/conduit may be employed to supply the required cryogenic fluid (or a precursor thereof) to the nozzle.

The stipulation "immediately prior to" the film making contact with said cryogen should be interpreted as indicating that the blast commences within 200 milliseconds prior to said contact, preferably within 100 milliseconds, and more preferably within 10-50 milliseconds.

These points will be elucidated in more detail below.

In a particular embodiment of the invention, the cryogenic fluid is a substantially dry cryogenic gas. In various tests, the inventors have observed that, in general, a gas is relatively easy to supply to and discharge from the nozzle, and that it is also relatively easy to prevent it from interfering (mixing) with the cryogen bath and/or clinging to the sample/sample holder. This is not to say that another form of cryogenic fluid cannot be used: for example, a fluid in liquid rather than gaseous form will generally have a significantly higher heat capacity, which may be advantageous in certain situations. However, the practical aspects (ease of use) set forth above will typically outweigh such an advantage. In order to prevent unwanted introduction of crystalline ice into the vicinity of the sample, the employed cryogenic gas should be substantially dry. For example, one could use Nitrogen gas at $-160°$ C. and with <10 ppm (and preferably even less) water vapor. Other gases—such as helium, xenon, argon, neon, etc.—could, in principle, also be used, but such gases tend to be more expensive and more difficult to handle than nitrogen.

In a particular aspect of the embodiment of the invention set forth in the previous paragraph, the cryogenic gas in said blast is caused to undergo substantially laminar flow along at least part of said second major surface. An advantage of such flow is that the gas makes substantially uniform thermal contact with the second major surface (and the interior of the aperture(s) within it) in a predictable and controllable manner, whereby (for example) the speed of the flow can be adjusted in order to influence the rate of thermal transfer from the sample to the cryogenic fluid, if desired. In contrast, a non-laminar/turbulent blast will tend to be less homogeneous, creating a risk that the blast may contain relatively low-pressure pockets in which thermal transfer from the sample to the blast is less than optimal, with an attendant risk of unwanted ice formation within such pockets. This is not to say that a non-laminar fluid blast cannot be used in the invention, but its stochastic/poorly controllable nature tends to make it a somewhat less attractive option.

If a gas is used as the cryogenic fluid, it will need to issue from the nozzle at a cryogenic temperature. Gas at a temperature above cryogenic levels (e.g. room-temperature gas) can, for example, be appropriately cooled by passing it through a heat exchanger (which term should be broadly interpreted as encompassing any suitable cooling device). Such a heat exchanger might, for example, comprise a hollow pipe that is wound into a coil within a vat; the vat can be filled (or flushed) with a cryogenic liquid (such as liquid nitrogen), and the gas to be cooled (such as nitrogen at room temperature) can be passed into and through the pipe, from which it will emerge at a reduced temperature. If the coiled pipe is sufficiently long and thin-walled, the liquid in the vat is cold enough and present/replenished in sufficient quantity, and the flow-rate of gas within the pipe is not too high, then gas emerging from the pipe will be at cryogenic temperature. If the gas emerges at non-cryogenic temperature, then a series-arrangement of such heat exchangers could be employed to perform multi-stage/cascade cooling, for example. In a different scenario, the heat exchanger could, for example, employ an adiabatic cooler, in which an input gas is cooled by allowing it to suddenly expand (e.g. using a piston-based mechanism). These and other alternative scenarios will be well within the ambit of the skilled artisan in the field of cryogenics. Ideally, the cooled product emerging from the heat exchanger will consist purely of cryogenic gas. However, if the temperature attained by the heat exchanger approaches the boiling/condensation point of the gas in question, then some of the input gas may emerge in (quasi-)liquid form, e.g. as a vapor or mist of liquid droplets; for example, in the case of nitrogen gas at 1 atmosphere pressure, such (partial) condensation into liquid will start to occur at temperatures around $-196°$ C. In this context, in a particular embodiment of the present invention, the gas supplied to the nozzle is cooled to a cryogenic temperature using a method that comprises the following steps:

Providing gas at a non-cryogenic temperature to an input of a heat exchanger;

Taking a gas/vapor mixture at a cryogenic temperature from an output of the heat exchanger, which vapor comprises condensed droplets of said gas;

Extracting cryogenic gas from said gas/vapor mixture, and using the extracted gas to produce said blast.

In a particular aspect of such an embodiment, the step of extracting cryogenic gas from said stream of gas/vapor mixture comprises at least one of the following procedures:

Sucking the gas out of the stream, in a direction substantially transverse to the stream;

Blowing the gas out of the stream, in a direction substantially transverse to the stream.

These approaches exploit the fact that the density of gas in the gas/vapor mixture will be less than that of the condensed droplets in the vapor, making it possible to use a pressure gradient to suck/blow gas laterally out of the stream while causing minimal lateral displacement of the droplets. Using these insights, various possible nozzle designs can be contemplated. For example:

(i) A first pipe with an annular cross-section could be used to guide the stream of mixed gas/vapor in a falling annular "curtain" perpendicular to, and centered upon, the backside of a circular sample holder. The inner diameter of said annular cross-section is somewhat larger than the diameter of the sample holder, so that this curtain tends to fall outside the perimeter of the sample holder. A second pipe is concentrically arranged along the cylindrical axis of the first pipe, with one end located just above the sample holder and the other end connected to an aspirator (suction device). This creates a circularly symmetric pressure gradient from the edges of the sample holder toward its center, and this pressure gradient draws cryogenic gas out of the annular curtain and causes it to flow over the backside surface of the sample holder toward and into the second pipe. This flow can be applied in the form of a blast by (for example) suddenly opening/closing a valve between the second pipe and the aspirator. See FIG. 4A, for example.

(ii) In a variant of such a design, the first pipe no longer needs to have an annular cross-section, and is located to one side of the sample holder (outside its perimeter); this creates a "tangential" curtain of falling gas/vapor mix. The second pipe is similarly shaped/sized/situated, except that it is located diametrically across from the first pipe (with respect to the center of the sample holder). In this case, an aspirator connected to the second pipe draws cryogenic gas out of the tangential curtain and causes it to flow over the interposed backside surface of the sample holder toward and into the second pipe. Once again, this flow can be applied in the form of a blast by (for example) suddenly opening/closing a valve between the second pipe and the aspirator. See FIG. 4B, for example.

The design and implementation of various other such embodiments will be well within the competence of the skilled artisan. For good order, FIG. 4C shows a situation similar to that in FIG. 4B, except that the product from the employed heat exchanger now comprises gas only, rather than a mix of gas and liquid droplets. Such a situation can, for example, be achieved using more accurate temperature regulation of the heat exchange process.

In order to achieve satisfactory vitrification of the backside of the aqueous liquid film, its exposure to cryogenic fluid from the nozzle of the current invention should be sudden—hence the term "blast". If exposure to the cryogenic fluid from the nozzle is more gradual/extended, then there is a risk that the backside of said film will (at least partially) freeze into crystalline form rather than solidifying amorphously—which is undesirable in the context of the current invention. The timing and duration of the inventive blast can be tuned/optimized in dependence on various factors, particularly the speed at which the sample is (vertically) plunged into the cryogen bath—which may typically be of the order of about 2-3 meters per second—but also parameters such as the temperature of the cryogenic fluid in the blast, the pressure/flow pattern produced by the nozzle, etc. As a rule of thumb, solely given here for the purpose of general guidance, the following parameters can be used in the current invention:

The blast commences at a time T prior to the film making contact with the cryogen in the bath, where T is selected to lie in the range 1-100 milliseconds.

The blast lasts for a duration $\Delta T$ of time, where $\Delta T$ is selected to lie in the range 1-100 milliseconds.

The skilled artisan will be able to choose his own values of T and $\Delta T$, tailored to the set-up and parameters pertaining to a given embodiment of the invention.

With reference to the discussion above, and particularly that in the previous paragraph, the current invention also provides an apparatus for plunge-cooling a sample that is provided on a substantially planar sample holder, the apparatus comprising:

An arm that can be used to grip an edge of said sample holder and retain it in a substantially horizontal orientation;

A container that can be at least partially filled with a bath of cryogen, such that said cryogen has an exposed upper surface at a given horizontal level;

A dropping mechanism that can be used to move said arm into said container, allowing a sample holder in said arm to be plunged below said horizontal level, with a frontside of the sample holder pointing downward, characterized in that the apparatus further comprises:

A dosing mechanism for applying a controllable blast of cryogenic fluid to a backside of said sample holder;

A controller connected to said dropping mechanism and said dosing mechanism, for timing said blast to occur immediately prior to the sample holder crossing said horizontal level.

With regard to such an apparatus, the following can be noted:

The arm may be any structure/appendage that can be used to hold the sample holder horizontally and that will fit within the perimeter of the container. The mechanism that it uses to grip the sample holder is open to choice: it may, for example, entail some sort of tweezers, or a magnetic clamp, or a pin that cooperates with a corresponding aperture on the sample holder, for instance.

The container may be any liquid-tight vessel that lends itself to holding a body of the selected cryogen, deep enough to allow the sample holder to be plunged to a desired depth (e.g. a few mm) and wide enough to accommodate entry of the arm/sample holder during plunging. It may be a (relatively small) dewar or flask, for example, or just an insulated (metal or ceramic) cup.

The dropping mechanism can take various forms. It may, for example, employ a free-fall mechanism, with a mechanical or electromagnetic release. Alternatively, it may employ some sort of a spring/elastic mechanism that can be selectively triggered so as to "catapult" the arm into the container. Or it may employ an actuator (such as that a piezo or linear motor) can be enacted to actively drive the arm into the container, etc.

The dosing mechanism will basically comprise some form of controllable nozzle that can be used to issue a blast (puff, spurt) of cryogenic fluid on command. One could, for example, envisage a valve-operated nozzle that co-moves with the arm and is directed at the backside of the sample holder during its descent into the container. Alternatively, one could, for instance, envisage a nozzle that is not located by default above the sample backside, but that is instead swept into location above/past the sample holder at a selectable instant; in this case, the required blast is delivered by virtue of the rapid/sudden motion of the nozzle past the sample holder. The nozzle may, for example, be connected to a reservoir of cryogenic fluid via a flexible tube/conduit, or it may have its own "on-board" (mini-)reservoir.

The controller may typically be some form of computer processor. It may decide the timing of the blast in different ways, e.g. simply on the basis of a previous calibration run (passive approach) or using the output of a measuring device (such as an optical encoder, interferometer, capacitive sensor, photodiode, etc.) to determine the commencement/duration of the blast based on real-time measurement of the (momentary) position/speed of the dropping arm/sample holder (active approach).

The skilled artisan will understand these points, and will be able to choose and enact various implementations according to the particulars of a given situation.

With respect to the cryogen bath into which the sample is plunged, there are various possible choices as regards the cryogen used. For example, various practitioners report using a liquid ethane/propane mix. In a particular embodiment of the invention, the cryogen in the bath comprises liquid ethane (without substantial quantities of other constituents) at a temperature in the range $-160°$ C. to $-183°$ C. When vitrifying a sample by plunge-cooling it, one can tend to adhere to a rule of "the colder the better". However, at temperatures below ca. $-183°$ C., the inventors have observed that liquid ethane tends to become so viscous as to start to impede the plunging process, e.g. by clinging to the sample holder. Temperatures above this level (e.g. $-178°$ C.) are therefore generally preferable.

The invention will now be elucidated in more detail on the basis of exemplary embodiments and the accompanying schematic drawings, in which:

FIG. 1A renders an elevational view of aspects of a prior-art apparatus for plunge-cooling a sample to a cryogenic temperature.

FIG. 1B shows the apparatus of FIG. 1A, after modification according to the current invention.

FIG. 2 renders a plan view (top), transverse cross-sectional view (middle) and enlarged detail view (bottom) of aspects of a particular embodiment of a sample holder that can be used to bear a sample comprising a film of aqueous liquid.

Figure 5:
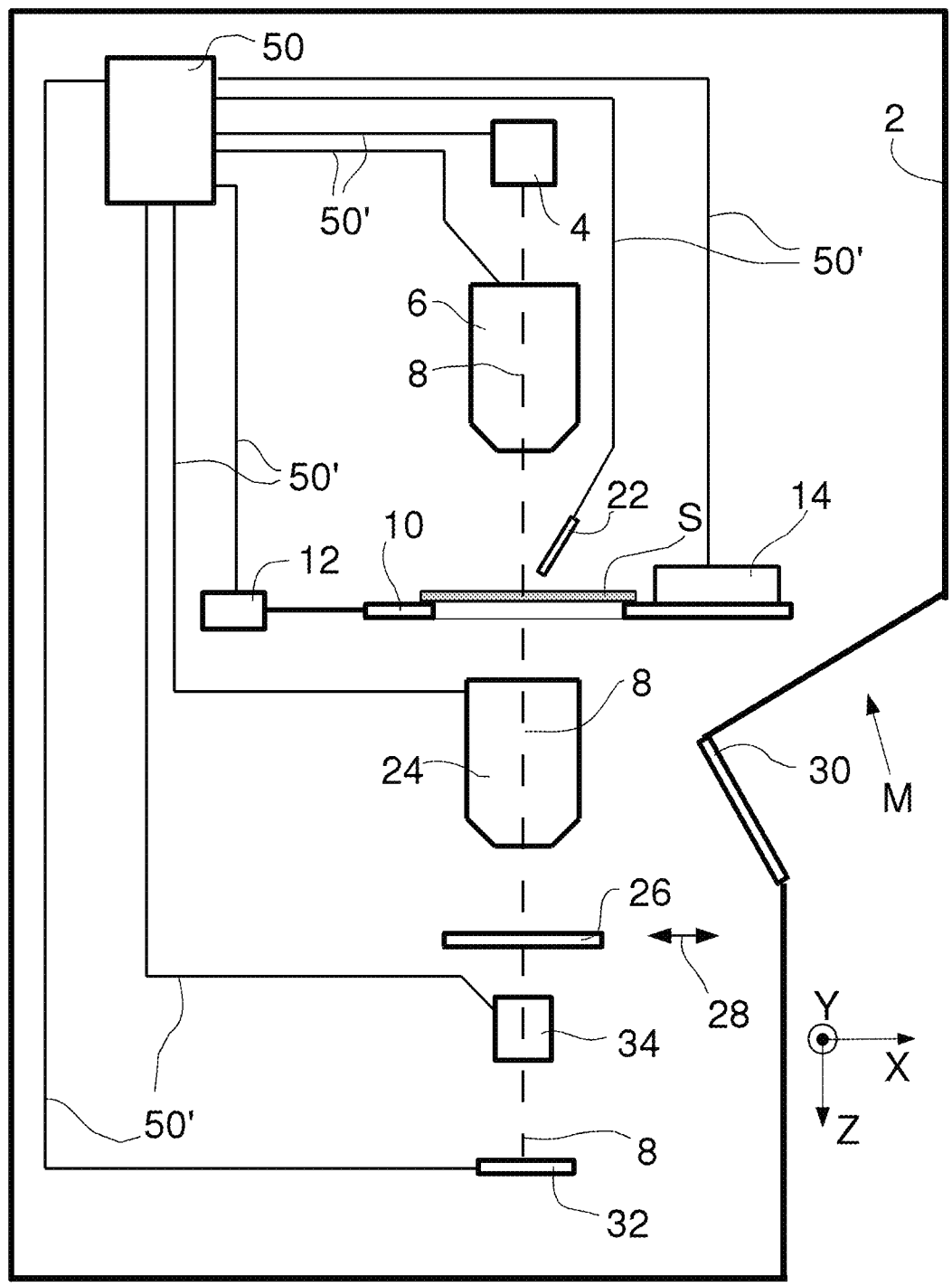

FIG. 5 renders an elevational view of a charged-particle microscope that lends itself to use with the current invention.

COMPARATIVE EXAMPLE

Prior Art

Figure 1A:
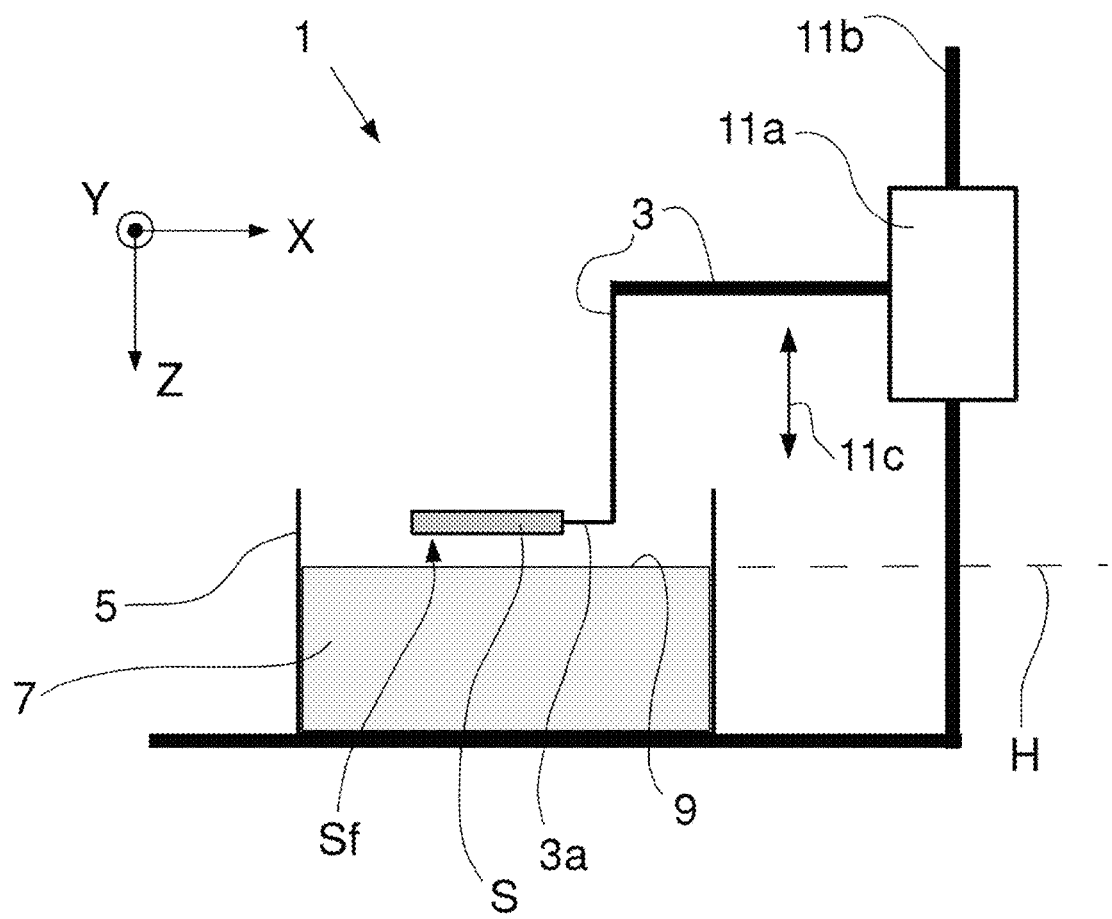
Figure 2:
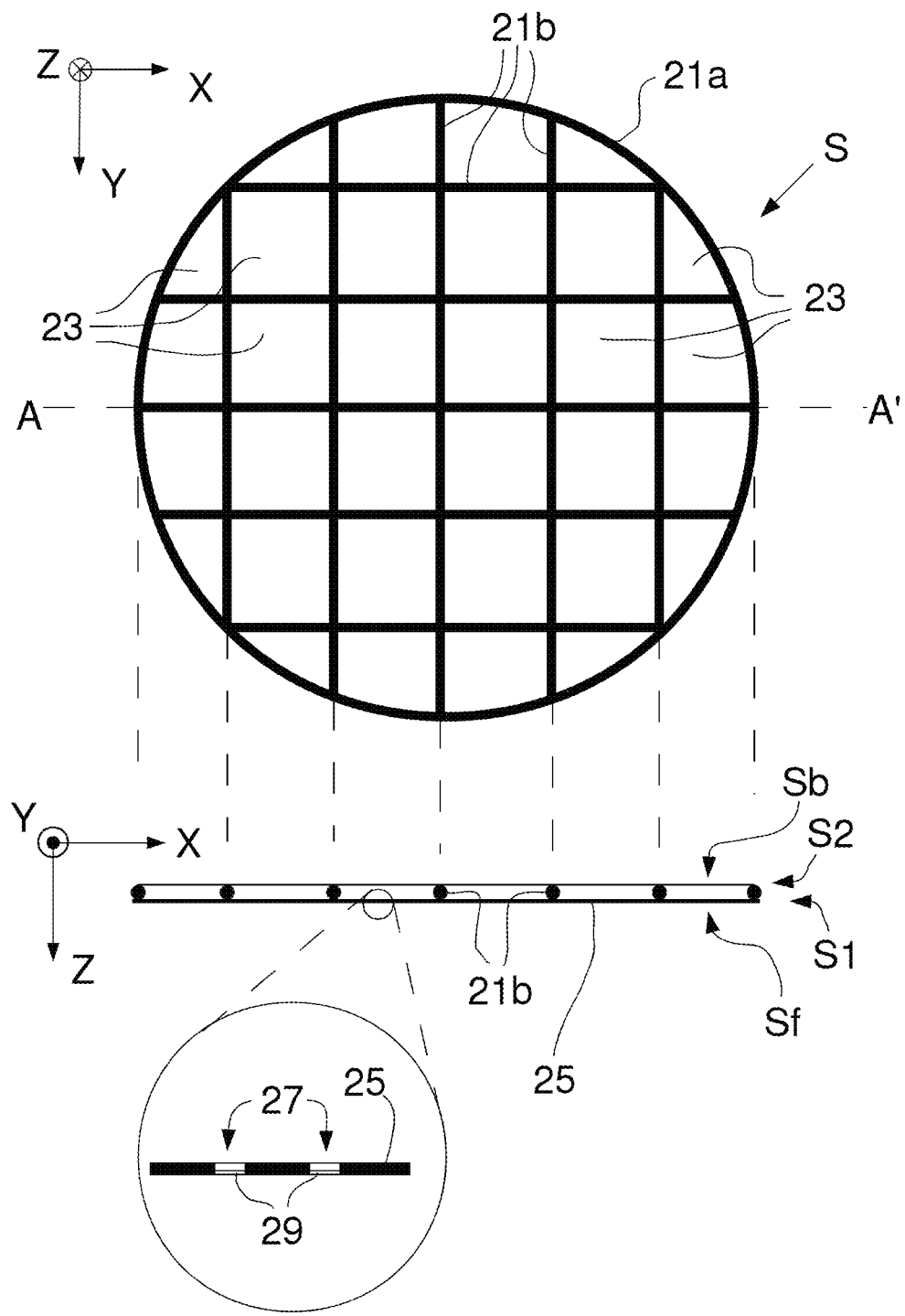

FIG. 1A renders a schematic elevational view of aspects of a prior-art apparatus 1 for plunge-cooling a sample to a cryogenic temperature, the sample being held on a sample holder S (shown in more detail in FIG. 2). Note the Cartesian coordinate system XYZ, which will be used in the following description. The depicted apparatus 1 comprises:

An arm 3 that can be used to grip the sample holder S at/proximal an edge thereof, and retain the sample holder S in a substantially horizontal orientation (parallel to the XY plane). This arm 3 comprises a gripping portion 3a that grips the sample holder S using, for example, a tweezers action. If desired, the sample holder S may have a small protruding lug (not depicted) that allows it to be more easily gripped by gripping portion 3a.

A container 5 (such as a dewar) that can be at least partially filled with a bath of cryogen 7, such that said cryogen 7 has an exposed upper surface 9 at a given horizontal level H. This upper surface 9 will be substantially horizontal, apart from relatively small meniscus effects.

A dropping mechanism 11a, 11b that can be used to (at least partially) move the arm 3 into said container 5, allowing a sample holder S in/on (the gripping portion 3a of) the arm 3 to be plunged below said horizontal level H, with a frontside Sf of the sample holder S pointing downward (parallel to the Z direction). As here depicted, the dropping mechanism 11a, 11b comprises a slider 11a that can move up and down along a rod 11b (as indicated by the arrows 11c), parallel to the Z direction. The downward motion of the slider 11a during the plunge may, for example, be free-fall, catapulted or motorized, as already set forth above. In the current set-up, a linear motor (not depicted) is provided in slider 11a, and this actuates itself along rod/stator 11b.

FIG. 2 (not to scale) renders more detailed (schematic) views of aspects of a particular embodiment of a sample holder S that can be used in conjunction with the apparatus 1 of FIG. 1A. This particular type of sample holder S is often referred to as a "grid" or "autogrid". It comprises a circular ring 21a of Cu wire, the diameter of the ring being ca. 3 mm and the diameter of the wire being of the order of about 50-100 µm (typically). Attached within the ring 21a are straight wire portions 21b, which are arranged to form an orthogonal grid pattern, thus defining a matrix-like array of (substantially square) apertures (openings/holes/windows) 23. The middle portion of FIG. 2 shows a transverse cross-sectional view of the upper portion of the Figure, taken along the diameter A-A'. It shows that the sample holder S has a substantially planar (plate-like) form, with opposed first (S1) and second (S2) major surfaces substantially parallel to one another. Any given aperture 23 "connects" these major surfaces S1, S2 in that it acts as a connecting passage between them. As here depicted, a membrane 25 has been spanned upon the first major surface S1 (and, optionally, affixed to the wires 21b, e.g. using an adhesive or by molten bonding). This membrane 25 may, for example, comprise a carbonaceous material such as nylon or graphene, and will typically have a thickness (in the Z direction) ranging from about 0.3 nm to hundreds of nm. The membrane 25 contains a distribution of perforations 27, which are clearly visible in the detailed view at the bottom of the Figure. These perforations 27 typically have a diameter (parallel to the XY plane) of the order of about 2 µm. In essence, the grid structure 21a, 21b acts as a scaffold for the membrane 25, and the membrane 25 in turn acts as a supporting structure for the perforations 27 (so that it is sometimes referred to as a "holey carbon support"). It is within the perforations 27 that the ultimate "sample" is to be provided and supported—in the form of a thin film 29 of aqueous liquid (comprising one or more study specimens suspended therein) that is spanned across each given perforation 27, remaining in place (inter alia) by virtue of surface tension effects. It should be noted that sample holders S as depicted in FIG. 2 (grid 21a, 21b+perforated membrane 25, 27) and as described above are commercially available, e.g. from firms such as Ted Pella, Inc., of Redding, Calif., USA. It is also possible to purchase (a variety of) pre-manufactured holey carbon films (corresponding to the perforated membrane 25, 27), e.g. from firms such as Quantifoil Micro Tools GmbH, Jena, Germany. It should be noted that, in principle, a sample holder S for use in the current invention basically requires only one aperture 23 and only one perforation 27; however, a plurality of these structures 23, 27 is certainly allowed by the invention, and is generally advantageous in that it typically allows more sample material to be present on a given area of the sample holder S.

A film 29 of aqueous liquid can be provided in the various perforations 27 of the sample holder S using methods well described in technical literature and known to the skilled artisan. In one such known method, a sheet of blotting paper (not depicted) is pressed against the surface S1 of the sample holder S, is then moistened with the aqueous liquid in question, and is subsequently removed (e.g. peeled off) of the sample holder S—causing (most of) the apertures 27 to be endowed with a (mini-)film 29 of the aqueous liquid, which is spanned within them by surface tension effects. A method of this type is described, for example, in the article *Cryo-negative Staining* by Marc Adrian et al. in Micron 29 (2-3), Elsevier Science Limited, 1998, pp. 145-160, and will not receive further attention here.

Returning now to FIG. 1, once the sample holder S has been provided with its film(s) 29 of aqueous liquid as set forth above, it can be mounted upon the gripping portion 3a of the arm 3, in such a manner that the membrane 25 on surface S1 faces down toward the container 5, thus forming a frontside Sf of the holder S (with the surface S2 forming a backside Sb). A suitable bath of cryogen 7 (e.g. liquid ethane) is provided in the container 5, and the dropping mechanism 11a, 11b is then used to suddenly plunge the sample holder S into the cryogen 7, e.g. at a speed of ca. 2 ms$^{-1}$. Such a procedure is, for example, described in the above-mentioned article by Kasas et al. After the sample holder S has been plunge-cooled in this manner, it is removed from the cryogen 7 and placed on/in a cryo-holder (not depicted) that can maintain it at cryogenic temperature until it undergoes study in a CPM.

Figure 3A:
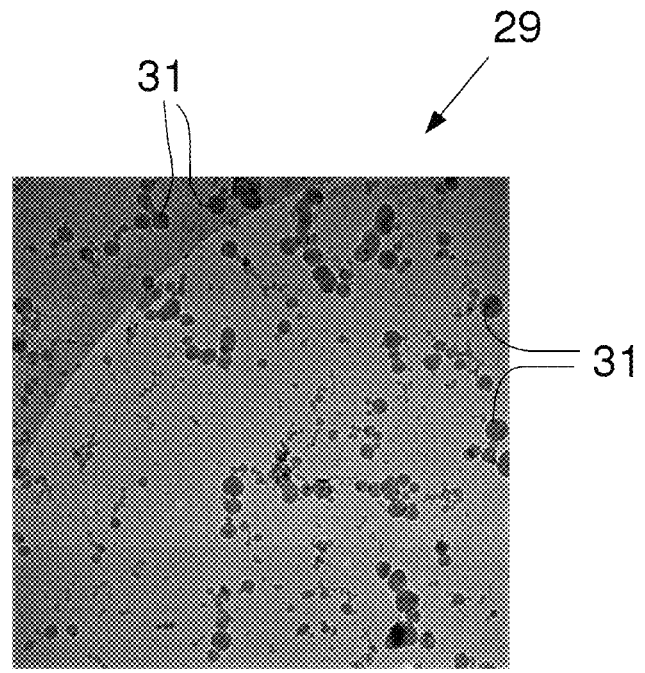
FIGS. 3A and 3B are relatively low-magnification TEM images of aqueous liquid samples prepared on a grid and vitrified using a plunging method according to the prior art (FIG. 3A) and the current invention (FIG. 3B).

As already set forth above, the inventors have found that this prior-art approach yields unsatisfactory results in terms of sample quality. More particularly, samples cooled in this manner tend to demonstrate serious contamination. This effect is shown in FIG. 3A, which depicts a 1 µm×1 µm square portion (tile) of a film 29 of aqueous liquid that has been plunge-cooled using a prior-art apparatus/technique as illustrated in FIG. 1A and set forth above, and that is here imaged using a cryo-TEM at relatively low magnification (too low to resolve the tiny biological study specimens suspended in the aqueous liquid in question). What should be an essentially homogeneous/featureless image is instead speckled with dark, dot-like features 31. As explained above, the inventors have established that these features 31 are, in fact, surfacial islands of ice that have formed on the side of the film 29 facing upward/away from the cryogen 7 during plunging. The presence of these features 31 obscures study specimens that share a common line-of-sight, and causes unwanted scattering effects in a charged-particle beam used to study the film 29.

Embodiment 1

Figure 1B:
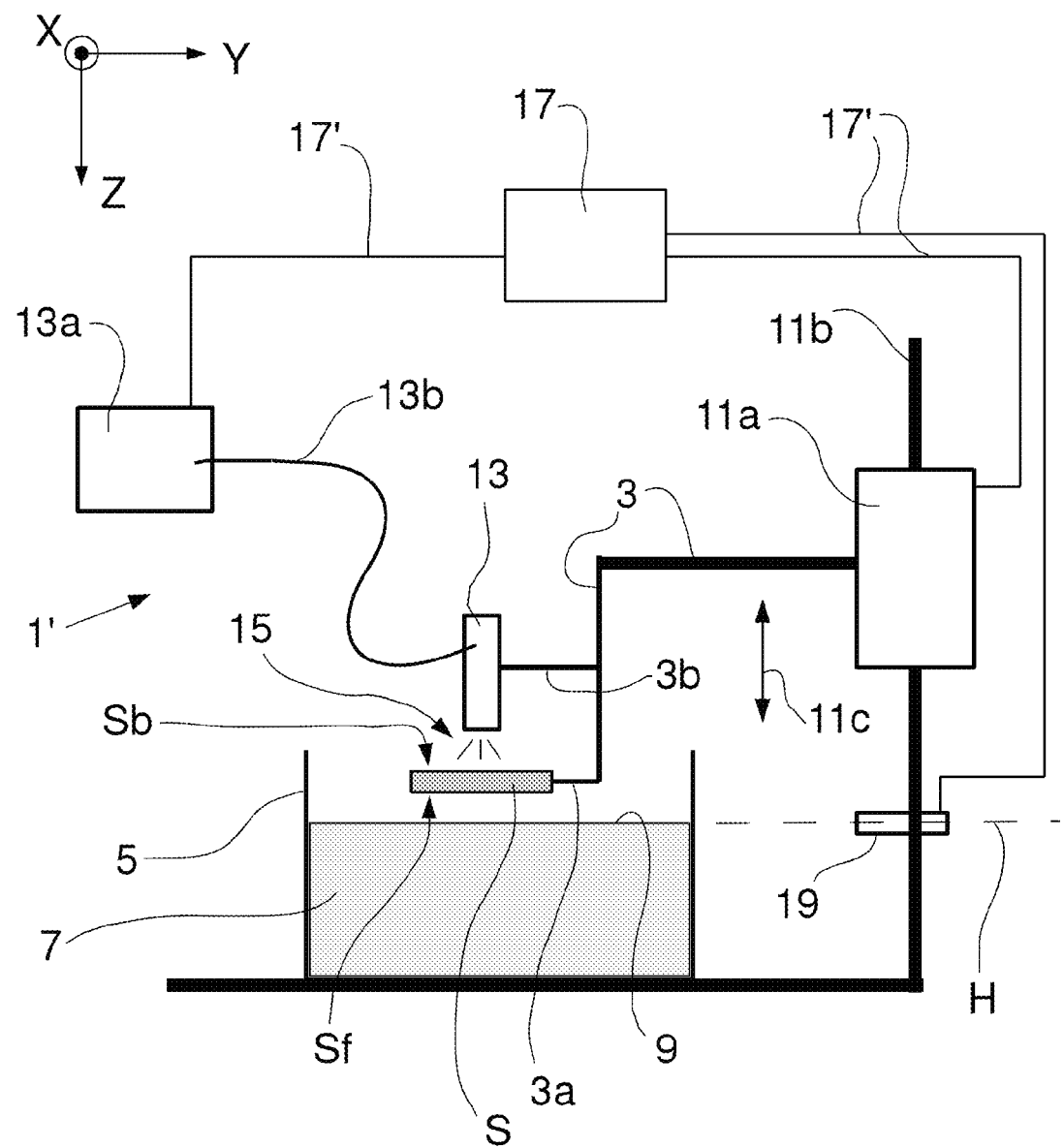

To address the negative issues set forth in the preceding Comparative Example (vis-à-vis contamination of the film 29), the present inventors modified the prior-art apparatus/technique described above. An example of a plunge-cooling apparatus 1' according to the current invention is shown in FIG. 1B. It shares many features with the apparatus of FIG. 1A (which are labeled using the same reference symbols), but it also contains many additional features/aspects.

In particular, the apparatus 1' comprises a nozzle 13 that is mounted on an appendage 3b of the arm 3 so that it points toward the backside Sb of the sample holder S, and can deliver a controlled blast 15 of cryogenic fluid thereto immediately before the frontside Sf of the sample holder reaches the horizontal level H. The nozzle 13 is connected to a production unit (heat exchanger/reservoir) 13a via a flexible tube/conduit 13b, and this production unit 13a can be used to produce/store a supply of cryogenic fluid required by the nozzle 13; in this case, the co-operating combination 13, 13a, 13b can be regarded as comprising a dosing mechanism for supplying the blast 15. The timing/duration of the blast 15 is governed by a controller 17 (e.g. a computer processor), which is connected to key elements of the apparatus 1' by control lines 17'. As here illustrated, the controller 17 is connected to:

The dosing mechanism 13, 13a, 13b, e.g. to a dosing valve or shutter that governs the flow of cryogenic fluid to/from an output of the nozzle 13;

The dropping mechanism 11a, 11b, e.g. to an actuator/release mechanism that sets the slider 11a in downward motion;

A device 19 that is used to determine when the sample holder S is about to cross the horizontal level H. Such a device 19 might, for example, comprise an optical encoder, or a photodiode that cooperates with a light beam that will be interrupted by the fall of the sample holder S, or a camera that uses image recognition software to recognize the position of the sample holder S (or a given part of the arm 3), etc. If desired, the device 19 may also be used to determine the speed of fall of the sample holder S during its plunge.

As already stated above, the device 19 is actually optional; as an alternative, one could predict the moment at which the horizontal level H will be crossed by the sample holder S on the basis of a prior calibration run, for instance. If desired, one can endeavor to keep the horizontal level H substantially constant, e.g. by embodying the container 5 as an "overflowing cup" into/out of which a stream of cryogen 7 is constantly flowing.

In a particular (non-limiting) example:
The sample holder S crosses the level H at 2 ms-1.
The nozzle 13 applies a blast of cryogenic gas commencing 1-10 milliseconds (T) before the level H is crossed and lasting for a duration 1-10 milliseconds (ΔT).
The cryogenic fluid employed in the blast 15 is dry nitrogen gas at −160° C. and at a pressure of 100-1000 mbar/flow rate of 0.1-3 liters per minute.
The (outlet of the) nozzle 13 is located 0.2-2 mm above the backside Sb of the sample holder S.

Figure 3B:
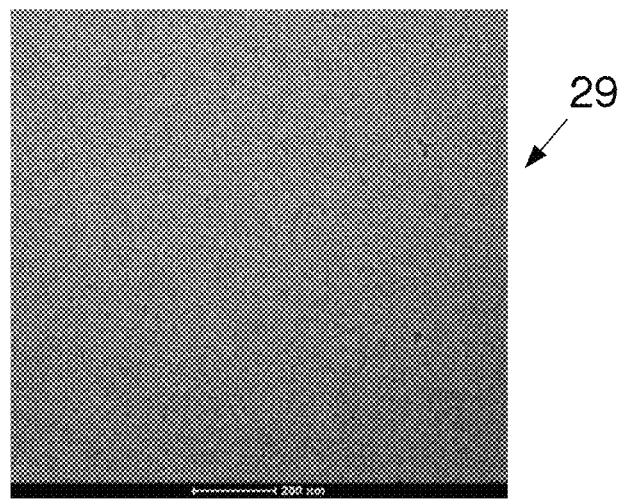

As already stated above, the effect of the blast 15 according to the present invention is to vitrify the upward-facing side of the film 29 just before the downward-facing side of the film 29 contacts the cryogen 7 in the container 5, thus forming a sealing layer that prevents water from leaching out of said upward-facing side. The ultimate effect of this sealing layer is to prevent the formation of the above-mentioned surfacial islands of ice on film 29. This effect is dramatically illustrated by FIG. 3B, which depicts a 1 μm×1 μm square portion (tile) of a film 29 of aqueous liquid that has been plunge-cooled using an apparatus/technique as illustrated in FIG. 1B and set forth in the current Embodiment, and that is imaged using a cryo-TEM at the same magnification (30 k) as in FIG. 3A. Notice the absence of the dark features 31 that are so prevalent in FIG. 3A.

Note that, after the sample holder S has been plunged into and taken out of the bath of cryogen 7 and before it is placed in a cryo-holder for subsequent storage/transport, it can be a good idea to tilt it briefly so as to allow any excess cryogen that may be present thereon to run off.

Embodiment 2

Figure 4A:
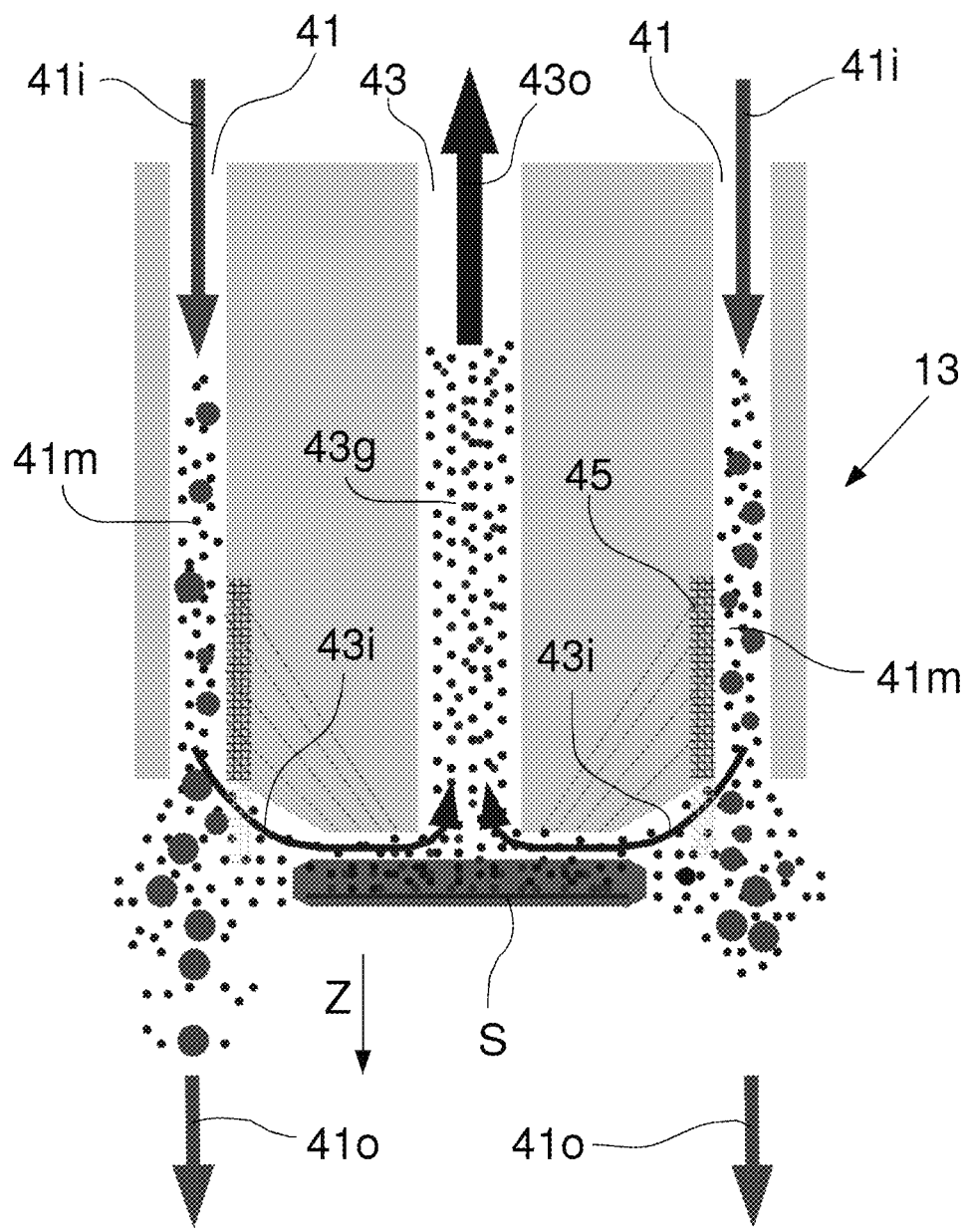
FIGS. 4A, 4B and 4C depict longitudinal cross-sectional views of different nozzle/flow architectures that lend themselves to application in embodiments of the current invention.

FIG. 4A renders a longitudinal cross-sectional view of a particular embodiment of a nozzle 13 suitable for use with the current invention. The depicted nozzle 13 is of a type (i) as set forth above, and comprises:

A first pipe (bore/channel/passage) 41 with an annular cross-section, centered upon the backside of a circular sample holder S and with an inner diameter somewhat larger than the diameter of the sample holder S. This pipe 41 has an input flow 41i (e.g. from a tube 13b as shown in FIG. 1B) and a (main) output flow 41o. In this particular embodiment, the input flow 41i comprises a stream 41m of mixed gas/liquid droplets that falls in an annular "curtain" parallel to the Z direction, and (mainly) passes outside the perimeter of the sample holder S.

A second pipe (bore/channel/passage) 43 that is concentrically arranged along the cylindrical axis of the first pipe 41, with one end located just above the sample holder S and the other end connected to an aspirator/suction device (not depicted). This arrangement creates a circularly symmetric pressure gradient from the edges of the sample holder S toward its center, and this pressure gradient draws cryogenic gas (but not condensed droplets) out of the annular stream 41m and causes it to flow over the backside surface of the sample holder S toward and into the second pipe 43, thus forming an input flow 43i of cryogenic gas 43g to the pipe 43 and a corresponding output flow 43o to the aspirator.

The flow 43i of cryogenic gas 43g can be applied in the form of a blast by (for example) suddenly opening/closing:
An output valve between the second pipe 43 and the aspirator; or
An input valve upstream of the first pipe 41.

Alternatively, one could employ an "advance and withdraw" strategy, whereby the nozzle 13 is briefly swept/pushed into position above the backside Sb of the sample holder S, momentarily putting it in location to deliver a brief dose of cryogenic gas 43i/43g.

FIG. 4A also illustrates optional meshes 45, which (if desired) can be used to assist the process of tapping off the gas stream 43g from the mixed stream 41m.

Embodiment 3

Figure 4B:
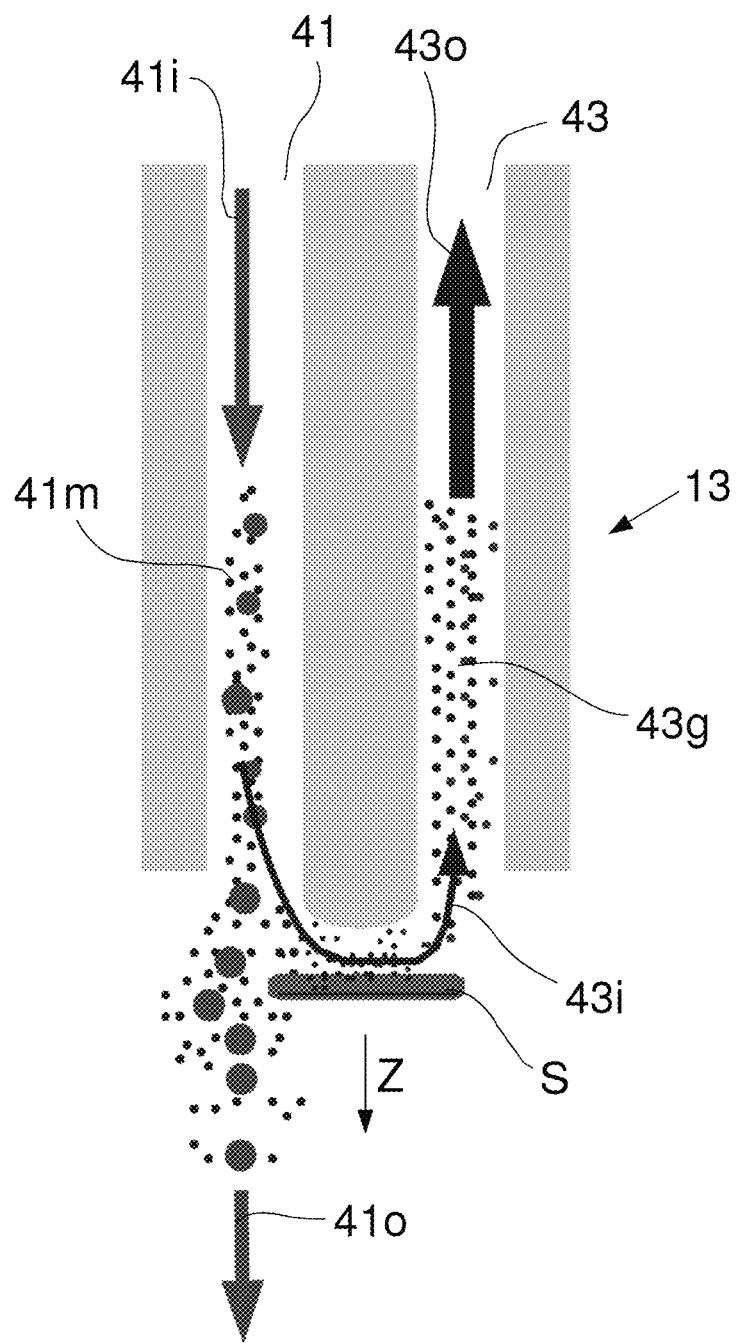

FIG. 4B renders a longitudinal cross-sectional view of an alternative embodiment of a nozzle 13 suitable for use with the current invention. The depicted nozzle 13 is of a type (ii) as set forth above, and comprises:

A first pipe 41 (that does not need to have an annular cross-section) located to one side of the sample holder S (outside its perimeter). This pipe 41 has an input flow 41i (e.g. from a tube 13b as shown in FIG. 1B) and an output flow 41o. Once again, the input flow 41i comprises a stream 41m of mixed gas/liquid droplets, and this falls in a tangential "curtain" parallel to the Z direction, passing outside the perimeter of the sample holder S.

A second pipe 43 that is similarly shaped/sized/situated, except that it is located diametrically across from the first pipe 41 (with respect to the center of the sample holder S). An aspirator (not depicted) is connected to the second pipe 43, and this draws cryogenic gas 43g (without condensed droplets) out of the tangential curtain 41m, causing a flow 43i over the interposed backside surface of the sample holder S and into the second pipe 43 (from which it eventually emerges as output flow 43o to the aspirator).

Once again, the flow 43i of cryogenic gas 43g can be applied in the form of a blast by (for example) suddenly opening/closing:

An output valve between the second pipe 43 and the aspirator; or

An input valve upstream of the first pipe 41.

As explained above, one could alternatively employ said "advance and withdraw" strategy, whereby the nozzle 13 is briefly swept/pushed into position above the backside Sb of the sample holder S, momentarily putting it in location to deliver a brief dose of cryogenic gas 43i/43g.

Embodiment 4

Figure 4C:
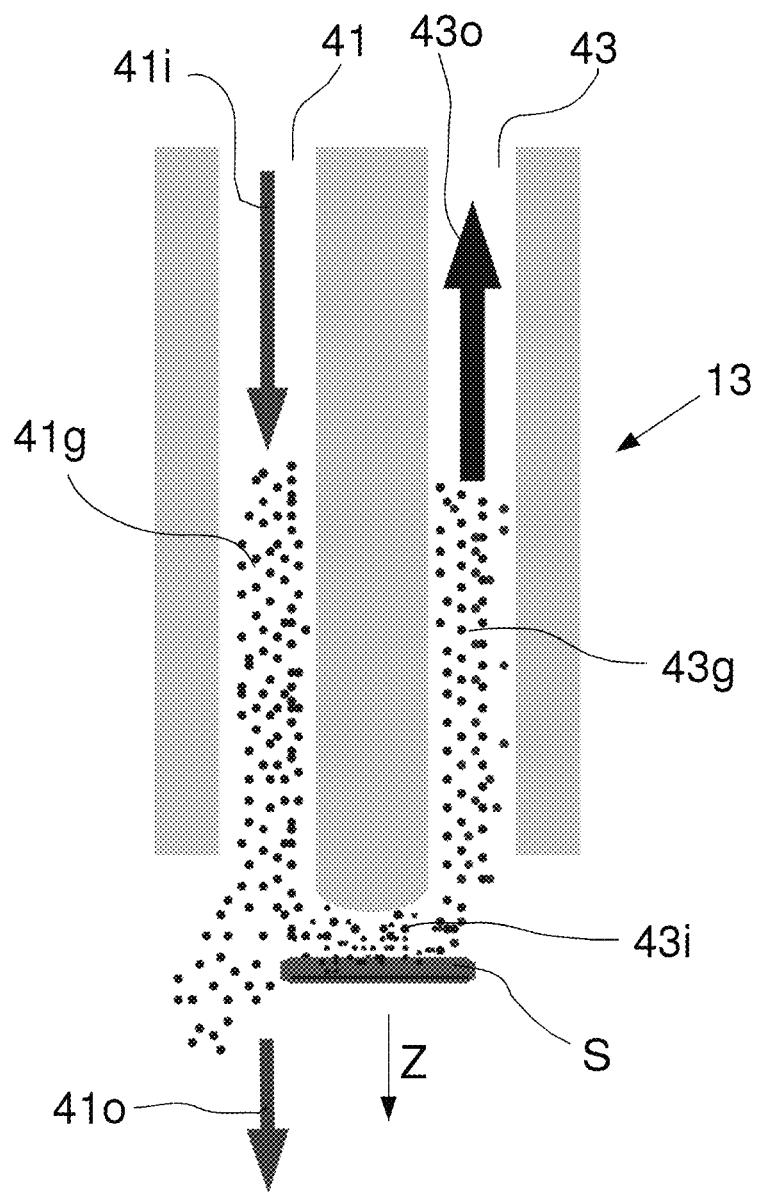

FIG. 4C shows a situation that is similar to that of FIG. 4B, except in that the input flow 41i now comprises cryogenic gas 41g rather than a mixture of gas/liquid droplets. This difference may, for example, be a result of more efficient temperature control in the production unit 13a of FIG. 1B, whereby the gas 41g is cooled to cryogenic temperatures, but not to a temperature too near its boiling/condensation point (−196° C. in the case of nitrogen gas).

Embodiment 5

FIG. 5 is a highly schematic depiction of an embodiment of a charged-particle microscope M that lends itself to use in conjunction with the current invention. In the Figure, a vacuum enclosure 2 encapsulates a CPM, which in this case is a TEM. In the depicted TEM, an electron source 4 (such as a Schottky gun, for example) produces a beam of electrons that traverse an electron-optical column 6, serving to direct/focus them onto a chosen region of a sample holder S (e.g. of a type as depicted in FIG. 2). This electron-optical column 6 has an electron-optical axis 8, and will generally comprise a variety of electrostatic/magnetic lenses, deflectors, correctors (such as stigmators), etc. In the case of a TEM, the electron-optical column 6 may be referred to as (comprising) a condenser system.

The sample holder S is held on a supporting device 10 than can be positioned in multiple degrees of freedom by a positioning device (stage) 12; for example, the supporting device 10 may comprise a finger that can be moved (inter alia) in the XY plane (see the depicted Cartesian coordinate system). Such movement allows different regions of the sample holder S to be irradiated/imaged/inspected by the electron beam traveling along axis 8, and also allows scanning motion to be performed in STEM mode. A cooling device 14 is in intimate thermal contact with the supporting device 10, and is capable of maintaining the latter at cryogenic temperatures. Thus, a sample holder S that is plunge-cooled to a cryogenic temperature in accordance with the current invention can be transferred to the CPM M using a (commercially available) cryoholder (which keeps it at cryogenic temperature), and can be placed for inspection on the supporting device 10, which has been pre-cooled by cooling device 14. The cooling device 14 may, for example, use a circulating cryogenic coolant to achieve and maintain a desired low temperature.

The focused electron beam traveling along axis 8 will interact with a sample (film(s) 29 of aqueous liquid) on the sample holder S in such a manner as to cause various types of "stimulated" radiation to be emitted from the sample, including (for example) secondary electrons, backscattered electrons, X-rays and optical radiation (cathodoluminescence); if desired, one or more of these radiation types can be detected with the aid of detector 22, which might be a combined scintillator/photomultiplier or EDX (Energy-Dispersive X-Ray Spectroscopy) detector, for instance. However, of predominant interest in a TEM are electrons that pass through the sample, emerge from it and continue to propagate along axis 8. Such transmitted electrons enter an electron-optical projection system 24, which will generally comprise a variety of electrostatic/magnetic lenses, deflectors, correctors (such as stigmators), etc. This lens system 24 focuses the transmitted electrons onto a fluorescent screen 26, which, if desired, can be retracted/withdrawn (as schematically indicated by arrows 28) so as to get it out of the way of axis 8. An image of (part of) the sample will be formed by lens system 24 on screen 26, and this may be viewed through viewing port 30 located in a suitable portion of the wall 2. The retraction mechanism for screen 26 may, for example, be mechanical and/or electrical in nature, and is not depicted here.

As an alternative to viewing an image on screen 26, one can instead make use of pixelated electron detector 32, such as a CMOS or CCD detector, for example. To this end, screen 26 is retracted (see previous paragraph), and electron-optical system 34 is enacted so as to shift the focus of the electrons emerging from lens system 24 and re-direct/focus them onto detector 32 (instead of screen 26). Here, the electrons can form an image that can be processed by controller 50 and displayed on a display device (not depicted), such as a flat panel display, for example. Alternatively, electron-optical system 34 can play the role of an EELS deflector, for example, serving to split the beam of electrons from lens system 24 into a plurality of (energy-selected) sub-beams, which impinge on different regions of detector 32. As yet another alternative, the detector 32 may be used to register a diffraction pattern produced by sample S, for example. The skilled artisan will be very familiar with these various possibilities, which require no further elucidation here. He will also realize that, if desired, detector 22 may be a pixelated detector of a type similar/identical to detector 32.

Note that the controller (computer processor) 50 is connected to various illustrated components via control lines (buses) 50'. This controller 50 can provide a variety of functions, such as synchronizing actions, providing setpoints, processing signals, performing calculations, and displaying messages/information on a display device (not depicted). The skilled artisan will understand that the interior of the enclosure 2 does not have to be kept at a strict vacuum; for example, in a so-called "Environmental TEM", a background atmosphere of a given gas is deliberately introduced/maintained within the enclosure 2.

For some general information regarding this subject matter, reference is made to the following links:

http://en.wikipedia.org/wiki/Electron_optics
http://en.wikipedia.org/wiki/Electron_microscope

We claim as follows:

1. A method of preparing a sample for study in a charged-particle microscope, comprising the following steps:
   providing a substantially plate-like sample holder having opposed first and second major surfaces substantially parallel to one another, comprising at least one aperture that connects said major surfaces and across which a membrane has been spanned upon said first major surface, which membrane comprises at least one perforation;
   spanning a film of aqueous liquid across said perforation, which liquid comprises at least one study specimen suspended therein;
   plunging the sample holder onto a bath of cryogen, whereby the sample holder is held with said first major surface pointing toward the cryogen and arranged substantially parallel to an exposed surface of the cryogen; and
   applying a blast of cryogenic fluid to said film from a nozzle pointing toward said second major surface, immediately prior to the film making contact with said cryogen.

2. The method of claim 1, wherein said cryogenic fluid is a substantially dry cryogenic gas.

3. The method of claim 2, wherein the cryogenic gas in said blast is caused to undergo substantially laminar flow along at least part of said second major surface.

4. The method of claim 2, wherein said gas is provided at a cryogenic temperature using a method that comprises the following steps:
   providing gas at a non-cryogenic temperature to an input of a heat exchanger;
   taking a stream of gas/vapor mixture at a cryogenic temperature from an output of the heat exchanger, which vapor comprises condensed droplets of said gas;
   extracting cryogenic gas from said stream, and using the extracted gas to produce said blast.

5. The method of claim 4, wherein said step of extracting cryogenic gas from said stream comprises at least one of the following procedures:
   sucking the gas out of the stream, in a direction substantially transverse to the stream;
   blowing the gas out of the stream, in a direction substantially transverse to the stream.

6. The method of claim 1, wherein said blast commences at a time T prior to said film making contact with said cryogen, where T is selected to lie in the range 1-100 milliseconds.

7. The method of claim 1, wherein said blast lasts for a duration $\Delta T$ of time, where $\Delta T$ is selected to lie in the range 1-100 milliseconds.

8. The method of claim 1, wherein said cryogen comprises liquid ethane at a temperature in the range $-160°$ C. to $-183°$ C.

9. An apparatus for plunge-cooling a sample for study in a charged-particle microscope, which sample is provided on a substantially planar sample holder, the apparatus comprising:
   an arm that can be used to grip an edge of said sample holder and retain it in a substantially horizontal orientation;
   a container that can be at least partially filled with a bath of cryogen, such that said cryogen has an exposed upper surface at a given horizontal level;
   a dropping mechanism that can be used to move said arm into said container, allowing a sample holder in said arm to be plunged below said horizontal level, with a front side of the sample holder pointing downward; and
   a dosing mechanism for applying a controllable blast of cryogenic fluid to a backside of said sample holder;
   a controller connected to said dropping mechanism and said dosing mechanism, for timing said blast to occur immediately prior to the sample holder crossing said horizontal level.

10. A method of examining a sample in a charged-particle microscope, which microscope comprises:
    a charged-particle source for producing a beam of charged particles;
    a supporting device for supporting a sample holder on which the sample is mounted;
    a cooling device for maintaining said sample holder at a cryogenic temperature at least while it is on said supporting device;
    a particle-optical column for directing said beam onto and through said sample, so as to form an image of part of the sample on a detector,
    characterized in that, prior to being placed on said supporting device, the sample is prepared using a method of claim 1.

11. A method of preparing a sample for observation in a charged particle beam system, comprising:
    providing a sample holder having a first major surface and an opposing second major surface, the sample holder supporting a sample having containing one or more specimens of interest;
    orienting the sample holder with the first major surface facing toward a cryogenic bath and the second major surface facing away from the cryogenic bath;
    applying a cryogenic fluid to the second major surface of the sample holder;
    plunging the sample holder into the cryogen bath immediately after applying the cryogenic fluid to the second major surface.

12. The method of claim 11, in which the application of the cryogenic fluid cools the sample quickly enough to freeze in an amorphous state the sample face facing away from the cryogen bath.

13. The method of claim 11, in which the cryogenic fluid comprises a substantially dry cryogenic gas.

14. The method of claim 13, wherein the cryogenic gas is generated by:
    supplying gas at a non-cryogenic temperature to a gas inlet of a heat exchanger, said heat exchanger maintained at a cryogenic temperature;
    extracting a stream of fluid from the output of said heat exchanger, comprising cryogenic gas or cryogenic gas and condensed cryogenic liquid, said liquid, if present, having the same composition as the gas;
    separating said cryogenic gas from any cryogenic liquid present; and
    using said cryogenic gas for said cryogenic fluid blast.

15. The method of claim 14, in which said separation of cryogenic gas from any cryogenic liquid present is performed by sucking gas out of the stream, in a direction substantially transverse to the stream or blowing gas out of the stream, in a direction substantially transverse to the stream.

16. The method of claim 13, in which the cryogenic gas is directed to undergo substantially laminar flow across at least part of the sample face.

17. The method of claim 11, in which application of the cryogenic fluid lasts for a duration of time $\Delta T$, where $\Delta T$ is selected to last for a range of 1-100 milliseconds.

18. The method of claim 11, in which the application of the cryogenic fluid commences at a time T prior to said sample making contact with said cryogen bath, where T is selected to lie in the range 1-100 milliseconds.

19. The method of claim 11, in which said cryogen bath comprises liquid ethane at a temperature in the range of −160° C. to −183° C.

20. The method of claim 11, in which said cryogenic fluid for said blast comprises nitrogen.

* * * * *